United States Patent [19]

Gehrer et al.

[11] Patent Number: 5,306,847
[45] Date of Patent: Apr. 26, 1994

[54] MANUFACTURE OF 1,2-PROPYLENE GLYCOL

[75] Inventors: Eugen Gehrer, Ludwigshafen; Wolfgang Harder, Weinheim, both of Fed. Rep. of Germany

[73] Assignee: BASF Aktiengesellschaft, Ludwigshafen, Fed. Rep. of Germany

[21] Appl. No.: 981,318

[22] Filed: Nov. 25, 1992

[30] Foreign Application Priority Data

Nov. 26, 1991 [DE] Fed. Rep. of Germany ....... 4138792

[51] Int. Cl.$^5$ ................ C07C 29/132; C07C 31/18
[52] U.S. Cl. .................... 568/863; 568/861; 568/862
[58] Field of Search ................ 568/861, 862, 863

[56] References Cited

U.S. PATENT DOCUMENTS

| 3,449,445 | 6/1969 | Wetherill | 260/635 |
|---|---|---|---|
| 3,715,388 | 2/1973 | Valbert | 260/497 |
| 3,935,284 | 1/1976 | Kruse | 260/635 |
| 4,024,193 | 5/1977 | Kruse | 260/618 |
| 4,517,391 | 5/1985 | Schuster et al. | 568/885 |
| 4,960,960 | 10/1990 | Harrison et al. | 568/863 |
| 5,097,089 | 3/1992 | Gracey et al. | 568/863 |
| 5,107,018 | 4/1992 | Schuster | 568/863 |

FOREIGN PATENT DOCUMENTS

| 2025829 | 3/1991 | Canada . |
|---|---|---|
| 0100406 | 2/1984 | European Pat. Off. . |
| 0044444 | 4/1984 | European Pat. Off. . |
| 0147219 | 3/1989 | European Pat. Off. . |
| 0306215 | 3/1989 | European Pat. Off. . |
| 0405956 | 1/1991 | European Pat. Off. . |
| 0410613 | 1/1991 | European Pat. Off. . |
| 524101 | 4/1931 | Fed. Rep. of Germany . |
| 541362 | 12/1931 | Fed. Rep. of Germany . |
| 2321101 | 11/1974 | Fed. Rep. of Germany . |
| 2366264 | 4/1980 | Fed. Rep. of Germany . |
| 3904083 | 8/1990 | Fed. Rep. of Germany . |
| 0415202 | 3/1991 | Fed. Rep. of Germany . |
| 3932332 | 4/1991 | Fed. Rep. of Germany . |
| 299373 | 3/1930 | United Kingdom . |
| 1450700 | 9/1976 | United Kingdom . |

OTHER PUBLICATIONS

Chem. Abst., vol. 90, 1979, 5845X.(Sokolova et al.).
Z. Phys. Chem., Abt. A, 159, 337 (1932).(Schmidt, D).
J. Am. Chem. Soc., 54, 4678 (1932).(Connor et al.).
Weissermel and Arpe, Industrielle Organische Chemie, 2nd Ed., pp. 259-260, 251-258, Weinheim, 1978.
Claims (in English) for U.S. Ser. No. 07/910,056 as OZ 0050/42541.

Primary Examiner—Werren B. Lone
Attorney, Agent, or Firm—Keil & Weinkauf

[57] ABSTRACT

A process for the manufacture of 1,2-propylene glycol, wherein dihydroxyacetone is hydrogenolytically converted to 1,2-propylene glycol in a single stage using a catalyst.

5 Claims, No Drawings

MANUFACTURE OF 1,2-PROPYLENE GLYCOL

The present invention relates to a process for the preparation of 1,2-propylene glycol.

The catalytic hydrogenation of dihydroxyacetone, when carried out at temperatures ranging from 20° to 200° C., leads to the formation of glycerol (cf EP-A 405,956; EP-A 306,215; U.S. Pat. No. 3,935,284; U.S. Pat. No. 4,024,193; *Sb. Tr. Vsec. Zaochn. Politekn. Inst.* 100, 7 (1976)-C.A. 90, 5845 x). These references make no mention of the formation of 1,2-propylene glycol.

The catalytic hydrogenolysis of glycerol to 1,2-propylene glycol has also been disclosed (cf DE-PS 524,101; DE-PS 541,362; *Z. Phys. Chem.*, Section A 159, 337 (1932); *J. Am. Chem. Soc.*, 54, 4678 (1932)). This process demands the use of drastic reaction conditions at certain stages, in particular the use of high reaction temperatures, which cause extensive formation of decomposition products of glycerol, which in turn leads to losses of yield. Some of these decomposition products, particularly ethylene glycol, are difficult to separate from the 1,2-propylene glycol formed, by distillation methods. The yields obtained in all of these processes are poor or at best only moderate, so that they are unsuitable for use on an industrial scale.

Thus 1,2-propylene glycol, an important chemical used, for example, in antifreeze agents and brake fluids and as the diol component in the manufacture of polyurethanes and as the starting point for the manufacture of poly(propylene glycol)s, has hitherto been prepared industrially virtually only by the addition of water to 1,2-propylene oxide (cf K. Weissermel, H.-J. Arpe: *Industrielle Organische Chemie*, 2nd Edition, pp. 259 to 260, Verlag Chemie, Weinheim 1978). Other routes leading to the manufacture of 1,2-propylene glycol, such as the preparation from propene via 1,2-diacetoxypropane followed by saponification thereof (U.S. Pat. No. 3,715,388), either cannot be carried out on an industrial scale or are economically unfeasible, as is the case with the manufacture of 1,2-propylene glycol by hydrogenolysis of glycerol, on account of the drawbacks and problems mentioned above.

Since the starting material propylene oxide is not yet industrially available via the direct oxidation of propene and its manufacture by the chlorohydrin process involves wastewater and by-product problems, or its manufacture by any of the prior art cooxidation processes leads to the coproduction of other products such as acetic acid, methyl-tert-butyl ether, styrene or cyclohexanol, which is undesirable from an engineering viewpoint (cf K. Weissermel, H.-J. Arpe: *Industrielle Organische Chemie*, 2nd Edition, pp. 251 to 258, Verlag Chemie, Weinheim 1978), it is an object of the present invention to provide a process which enables 1,2-propylene glycol to be manufactured economically on an industrial scale using a basis other than propylene oxide as starting point.

Accordingly, we have found a process for the manufacture of 1,2-propylene glycol, wherein dihydroxyacetone is hydrogenolytically converted to 1,2-propylene glycol in a single stage using a catalyst.

The single-stage catalytic hydrogenolysis of dihydroxyacetone probably proceeds via the hitherto unknown sequence of reactions indicated in the following reaction scheme (1):

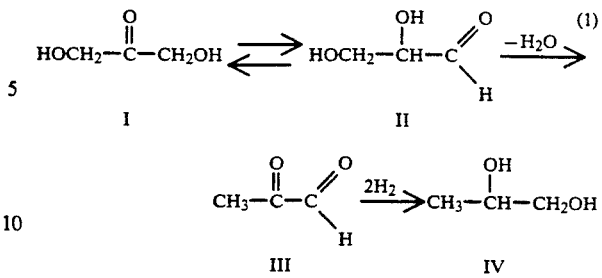

Presumably, under the reaction conditions used in this invention, water is eliminated from the tautomeric derivative glyceraldehyde II, which is in equilibrium with the dihydroxyacetone I, and this causes the formation of methyl glyoxal III, which is apparently instantaneously hydrogenated to the desired 1,2-propylene glycol IV. Although it has not yet been possible, under the reaction conditions used, to detect the postulated intermediates II and III in the reaction mixture on account of their evident instability under the reaction conditions used, the route indicated still seems to be plausible from the results of comparative experiments. Thus one can virtually rule out the possibilty of the formation of 1,2-propylene glycol being effected in the process of the invention via hydrogenolysis of glycerol formed as an intermediate. Under identical reaction conditions, there is only non-quantitative and slow conversion of glycerol to 1,2-propylene glycol with considerably poorer yield and selectivity. Thus by the expression "hydrogenolysis of dihydroxyacetone in a single stage" we mean the hydrogenolytic conversion of dihydroxyacetone to 1,2-propylene glycol under conditions such as allow for the hydrogenolysis of dihydroxyacetone to 1,2-propylene glycol by a direct route, that is to say, it is not necessary for the conversion to proceed via a stage involving the hydrogenolysis of the isolatable intermediate glycerol.

The process of the invention is generally carried out at temperatures above 200° C., preferably at temperatures ranging from 210° C., to 250° C., and under a hydrogen pressure generally of from 1 to 600 bar and preferably of from 50 to 200 bar, and more preferably under a hydrogen pressure of from 80 to 150 bar. The use of high temperatures, particularly temperatures above 200° C., is crucial to the success of the process of the invention, since dihydroxyacetone is mainly hydrogenated to glycerol at lower temperatures, and the hydrogenolysis of this latter compound to 1,2-propylene glycol takes place with lower yields and selectivities than the single-stage hydrogenolysis of dihydroxyacetone to 1,2-propylene glycol. At temperatures above 250° C. there is increasing formation of cleavage products such as ethylene glycol, propanol, methane, etc, for which reason the use of such higher temperatures is less preferred, although even at these high temperatures 1,2-propylene glycol is still formed in considerable quantities.

The process of the invention is preferably carried out using a heterogeneous catalyst. The heterogeneous catalyst is advantageously located in a fixed bed, through which the reaction mixture is passed upwardly from the base of the column or, preferably, downwardly in the form of a trickle stream. The process /f the invention is preferably carried out continuously, the period of contact between the reaction mixture and the catalyst advantageously being from 0.5 to 3 h and preferably from 0.75 to 1.5 h.

The hydrogenolysis of the dihydroxyacetone is generally carried out in solution, preference being given to polar solvents such as water or alcohols, preferably $C_1$–$C_{20}$ alcohols such as methanol, ethanol, propanol, isopropanol, butanols, 2-ethylhexanol, octanols, nonanols, decanols, hexadecanol, and octadecanol, and also polyhydric alcohols such as glycerol. A particularly preferred solvent is 1,2-propylene glycol, as this considerably simplifies the purification of the reaction product by distillation.

The hydrogenolysis of the dihydroxyacetone can be effected using virtually all types of hydrogenation catalysts, particularly those containing at least one element selected from Subgroups VI, VII, VIII, and/or I of the periodic table. The catalysts may be solid catalysts or in the form of supported catalysts, in which the support material may be, for example, activated charcoal, barium sulfate, calcium carbonate, silicon dioxide, aluminum oxide, zirconium dioxide, titanium dioxides, silicas, precipitated amorphous silicic acid, and/or silicates such as steatite. Particularly suitable catalysts are those containing one or more elements selected from the group comprising chromium, molybdenum, tungsten, manganese, rhenium, ruthenium, cobalt, rhodium, nickel, iron, palladium, platinum, copper, and silver.

The process of the invention may involve the use of hydrogenation catalysts comprising metals in activated, finely-divided form having a large surface area, e.g., Raney nickel, Raney cobalt, palladium sponge, or platinum sponge. Alternatively, the catalysts used in the process of the invention may contain the catalytically active metals deposited on a support material. Examples of such catalysts are the commercial hydrogenation catalysts palladium on activated charcoal, platinum on activated charcoal, ruthenium on activated charcoal, rhodium on activated charcoal, palladium on barium sulfate, palladium on barium carbonate, palladium on calcium carbonate, platinum on barium sulfate, platinum on barium carbonate, platinum on aluminum oxide, platinum on calcium carbonate, ruthenium on calcium carbonate, ruthenium on barium carbonate, ruthenium on barium sulfate, rhenium /n activate charcoal, etc.

The process of the invention may be carried out using for example so-called precipitated catalysts, if desired. Such catalysts can be prepared by precipitating their catalytically active components from solutions of their salts, in particular from solutions of their nitrates and/or acetates, this being effected, for example, by adding to such solutions solutions of alkali metal hydroxides and/or carbonates and/or solutions of alkaline-earth metal hydroxides and/or carbonates so that the precipitated metals are in the form of their diffcultly soluble hydroxides, oxide hydrates, basic salts or carbonates, after which the resulting precipitates are dried and then calcined, generally at a temperature of from 300° to 700° C. and preferably from 400° to 700° C., to form the corresponding oxides, mixed oxides and/or mixed-valence oxides, these then being treated in a stream of hydrogen at, usually, from 200° to 700° C. and preferably from 200° to 400° C. to be reduced to the corresponding metals and/or oxidic compounds of a low degree of oxidation and thus to be converted to the desired catalytically active form. When it is desired to prepare precipitated catalysts which contain a support material, the catalytically active components can be precipitated in the presence of the desired solid support material, which can have been added to the salt solution or previously precipitated therein. Alternatively, the catalytically active components and the support material may be advantageously precipitated from the salt solution concurrently.

Examples of catalysts which may be used in the process of the invention are those described in DE-A 3,932,332, U.S. Pat. No. 3,449,445, EP-A 44,444, EP-A 147,219, DE-A 3,904,083, DE-A 2,321,101, EP-A 415,202, DE-A 2,366,264, and EP-A 100,406. Particularly preferred catalysts are for example those mentioned in EP-A 100,406 and DE-A 2,366,264.

On completion of the reaction, the effluent containing 1,2-propylene glycol can be worked up in conventional manner by distillation at atmospheric pressure or under reduced pressure.

The starting material used in the process of the invention, dihydroxyacetone, can be obtained in various ways, for example by fermentation, by microbial oxidation of glycerol (cf C. Rainbow, A. H. Rose: *Biochemistry of Industrial Micro-organisms*, pp. 612–613, Academic Press, London 1963), or preferably by a chemical route, by the thiazolium ylid-catalyzed autocondensation of formaldehyde (cf EP-A 410,613). The dihydroxyacetone to be used in the process of the invention is very preferably prepared by a process in which the autocondensation of formaldehyde is carried out by means of a thiazolium ylid catalyst in the absence of acidic or basic compounds in an aprotic, polar solvent. Examples of suitable solvents of this kind are ethers such as tetrahydrofuran, dioxane, or trioxane, ethylene glycol dimethyl ether, ethylene glycol diethyl ether, diethylene glycol dimethyl ether, nitriles such as acetonitrile, amides such as N,N-dimethyl formamide, N,N-diethyl formamide, N,N-dipropyl formamide, N,N-dibutyl formamide, hexamethylphosphoric triamide, lactams such as N-methylpyrrolidone, N-ethylpyrrolidone, sulfoxides and sulfones, e.g., dimethyl sulfoxide and sulfolane.

Examples of catalyst that can be used for the manufacture of dihydroxyacetone from formaldehyde are thiazolium ylids of formula Va

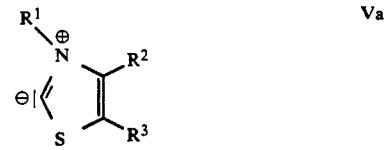

or benzothiazolium ylids of formula Vb

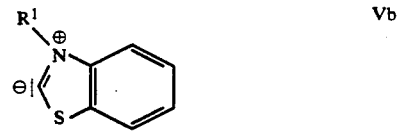

in which $R_1$ stands, e.g., for a $C_1$–$C_{30}$ alkyl group and preferably for a $C_2$–$C_{20}$ alkyl group or a halo-alkyl group of the same carbon number and containing, as halogen atoms, preferably fluorine or chlorine atoms, for a $C_1$–$C_{25}$ alkylene group attached to a polymeric carrier, for a $C_1$–$C_{20}$ aralkyl group and preferably a $C_7$–$C_{12}$ aralkyl group, in particular a benzyl group, or for an aryl group such as a phenyl or naphthyl group, and in which $R_2$ and $R_3$ are the same or different and each can stand for hydrogen, for a hydrogen atom, for a $C_1$–$C_{10}$ alkyl group and preferably a $C_1$–$C_4$ alkyl group, for a $C_7$–$C_{12}$ aralkyl group and preferably a benzyl group, or for a phenyl or naphthyl group. The radicals $R_1$, $R_2$, and $R_3$ may, if desired, carry substituents which are inert under the conditions of the reaction, for example alkyl groups, alkoxy groups, halogen atoms, $C_2$–$C_{10}$ dialkylamino groups, $C_1$–$C_{10}$ thioether groups, nitro groups, or nitrilo groups.

These thiazolium or benzothiazolium ylid catalysts can be produced from the corresponding thiazolium salts by reaction with an auxiliary base such as a tertiary amine. The production of the base-free and acid-free thiazolium ylid catalysts is preferably carried out by two different methods. One method is to produce the thiazolium ylid in a non-polar solvent, such as ethylene glycol dimethyl ether, which is a non-solvent for the salt of the auxiliary base formed during the production of the thiazolium ylid by reaction of a thiazolium salt with an auxiliary base, after which the precipitated salt of the auxiliary base is removed from the resulting catalyst solution by mechanical means, for example filtration or centrifugation. The other preferred method of producing the said base-free and acid-free thiazolium ylid catalysts comprises forming the thiazolium ylid in a polar solvent, such as dimethyl formamide, and separating it, by crystallization, from the soluble salt of the auxiliary base formed during the production of the thiazolium ylid from the corresponding thiazolium salt by means of an auxiliary base. Another possibility is to produce the thiazolium ylid catalyst in situ in the reaction mixture used for the preparation of dihydroxyacetone by the reaction of a N-formyl-N-alkyl-o-mercaptoaniline with a dehydrating agent such as an orthoformic acid ester.

This preferred method of manufacturing dihydroxyacetone produces dihydroxyacetone on the basis of a cheap starting material, i.e., formaldehyde, in yields of up to 94%. These preferred processes for the manufacture of dihydroxyacetone are the subject matter of German Patent Application P 41 22 669.0 and are described therein in detail.

The combination of the aforementioned method of manufacturing dihydroxyacetone with the process of the invention for the manufacture of 1,2-propylene glycol from dihydroxyacetone now makes it possible to effect low-cost large-scale production of 1,2-propylene glycol starting from formaldehyde as cheap raw material.

EXAMPLES

In Examples 1 to 5, use was made of a hydrogenation catalyst as described in EP-A 100,406 and having the following composition:
  66.0 wt % of Co, calculated as CoO,
  20.0 wt % of Cu, calculated as CuO,
  7.3 wt % of Mn, calculated as $Mn_3O_4$,
  3.6 wt % of Mo, calculated as $MoO_3$, and
  3.0 wt % of P, calculated as $H_3PO_4$.

The catalysts were activated before use by reduction with hydrogen at a temperature of 200° C. over a period of 12 h. In each case, the hydrogenolysis was carried out continuously in a tubular reactor. To determine the composition of the hydrogenolysis product once steady-state conditions had been set up, samples were taken from the reactor and subjected to gas chromatographic analysis following silylation.

EXAMPLES 1–4

The following examples show that when dihydroxyacetone is hydrogenated at a temperature above 200° C. the selectivity swings dramatically from being in favor /f glycerol to being in favor of 1,2-propylene glycol.

A 20 wt % solution of dihydroxyacetone in water was reacted with hydrogen under a pressure of 150 bar and at the temperature stated in Table 1 below, using the aforementioned catalyst. The throughput rate was 50 mL of dihydroxyacetone solution (50 mL of catalyst in 50 mL of reactor volume) per hour.

The results of the experiments are listed in Table 1 below.

TABLE 1

| EXAMPLE No. | Temperature [°C.] | Yield of propylene glycol [%] | Yield of glycerol [%] | Yield of ethylene glycol [%] |
|---|---|---|---|---|
| 1 | 120 | 2.6 | 96.7 | <0.1 |
| 2 | 150 | 11.2 | 89.3 | 0.15 |
| 3 | 180 | 15.6 | 74.0 | 0.47 |
| 4 | 210 | 89.2 | 6.3 | 3.7 |

EXAMPLE 5

This example shows that the hydrogenolysis of dihydroxyacetone to 1,2-propylene glycol must proceed via a different route from that involving intermediate glycerol, and that the hydrogenolysis of glycerol to 1,2-propylene glycol takes place under identical conditions much more slowly and with less pronounced selectivity than that of dihydroxyacetone.

Example 5 was carried out as described in Example 4 except that the dihydroxyacetone solution was replaced by a 20 wt % aqueous glycerol solution. There were obtained 43.7% of 1,2-propylene glycol, 16% of propanol, 1.2% of ethylene glycol, and small yields of other low alcohols. Under these conditions, 36.5% of the glycerol used as starting material remained unconverted.

EXAMPLE 6

This example demonstrates that the process of the invention for single-stage hydrogenolysis of dihydroxyacetone to 1,2-propylene glycol can also be carried out using other hydrogenation catalysts.

Dihydroxyacetone was converted to 1,2-propylene glycol in the manner described in Examples 1 to 4 and at the temperatures listed in Table 2 below, using a catalyst as described in DE-A 2,366,264 and containing
  55.6 wt % of Ni, calculated as NiO,
  15.3 wt % of Mg, calculated as MgO,
  25.6 wt % of Si, calculated as $SiO_2$,
  3.5 wt % of Mo, calculated as $MoO_3$.

The results are given in Table 2 below.

TABLE 2

| Temperature [°C.] | Yield of propylene glycol [%] | Yield of glycerol [%] | Unconverted dihydroxyacetone |
|---|---|---|---|
| 180 | 39.7 | 52.0 | — |
| 200 | 64.3 | 23.2 | — |
| 220 | 67.0 | 0.4 | — |

We claim:
1. A process for the manufacture of 1,2-propylene glycol, wherein dihydroxyacetone is hydrogenolyti- cally converted to 1,2-propylene glycol in the presence of a solvent using a heterogeneous hydrogenation catalyst at a temperature of above 200° C. and at a pressure of from 1 to 600 bar.

2. A process as claimed in claim 1, wherein the hydrogenolysis is carried out at temperatures above 200° C. but not exceeding 250° C.

3. A process as defined in claim 1, wherein the solvent used during hydrogenolysis of the dihydroxyacetone is selected from the group consisting of 1,2-propylene glycol, glycerol, water, a mixture of 1,2-propylene glycol and glycerol, a mixture of 1,2-propylene glycol and water and a mixture of 1,2-propylene glycol, glycerol and water.

4. A process as claimed in claim 1, wherein the dihydroxyacetone used is the product obtained from the autocondensation of formaldehyde in the presence of a thiazolium ylid catalyst.

5. A process as claimed in claim 1, wherein the catalyst used is one which contains at least one element selected from Subgroups VI, VII, VIII, and/or I of the periodic table.

* * * * *